US009662158B2

(12) United States Patent
Reiley (10) Patent No.: US 9,662,158 B2
(45) Date of Patent: May 30, 2017

(54) SYSTEMS AND METHODS FOR THE FIXATION OR FUSION OF BONE AT OR NEAR A SACROILIAC JOINT (75) Inventor: Mark A Reiley, Piedmont, CA (US)

(73) Assignee: SI-BONE INC., San Jose, CA (US)

(*) Notice: Subject to any disclaimer, the term of this patent is extended or adjusted under 35 U.S.C. 154(b) by 0 days.

(21) Appl. No.: 12/315,559

(22) Filed: Dec. 4, 2008

(65) Prior Publication Data
US 2009/0259261 A1 Oct. 15, 2009

Related U.S. Application Data (63) Continuation-in-part of application No. 11/653,504, filed on Jan. 16, 2007, now abandoned, which is a
(Continued)

(51) Int. Cl.
A61B 17/86 (2006.01)
A61B 17/84 (2006.01)
(Continued)

(52) U.S. Cl.
CPC ........ A61B 17/846 (2013.01); A61B 17/7055 (2013.01); A61B 17/8897 (2013.01); A61F 2/4455 (2013.01); A61B 17/1757 (2013.01); A61F 2/0077 (2013.01); A61F 2/28 (2013.01); A61F 2/30767 (2013.01); A61F 2/447 (2013.01); A61F 2/4465 (2013.01); A61F 2002/305 (2013.01); A61F 2002/3023 (2013.01); A61F 2002/30062 (2013.01);
(Continued)

(58) Field of Classification Search
USPC ............... 606/329, 96; 623/16.11, 17.16
See application file for complete search history.

(56) References Cited

U.S. PATENT DOCUMENTS 1,951,278 A * 3/1934 Ericsson .................. 606/67
2,136,471 A 11/1938 Schneider
(Continued)

FOREIGN PATENT DOCUMENTS

CN 1128944 A 8/1996
CN 1190882 A 8/1998
(Continued)

OTHER PUBLICATIONS

PCT International Preliminary Report on Patentability; PCT/US08/13351; Jan. 10, 2011.
(Continued)

Primary Examiner — Christian Sevilla
(74) Attorney, Agent, or Firm — Shay Glenn LLP (57) ABSTRACT At least one bone fixation device comprising a stem having a maximum outer diameter is inserted into the sacroiliac joint through a minimally invasive incision path sized approximately at or about the maximum outer diameter of the stem in soft tissue, into the iliac bone, across the sacroiliac joint and into the sacrum. The stem is inserted through the incision path to a position within the sacroiliac joint between the iliac bone and the sacrum, to fuse the sacroiliac joint, without invasive joint preparation, removal of cartilage, or scraping at or near the sacroiliac joint. Desirably, at least a portion of the stem includes a surface permitting bony in-growth.

8 Claims, 7 Drawing Sheets

Related U.S. Application Data continuation-in-part of application No. 11/136,141, filed on May 24, 2005, now Pat. No. 7,922,765, which is a continuation-in-part of application No. 10/914,629, filed on Aug. 9, 2004, now abandoned.

(60) Provisional application No. 61/000,166, filed on Oct. 24, 2007.

(51) Int. Cl.
    *A61B 17/70*     (2006.01)
    *A61F 2/44*     (2006.01)
    *A61B 17/88*     (2006.01)
    *A61B 17/17*     (2006.01)
    *A61F 2/00*     (2006.01)
    *A61F 2/28*     (2006.01)
    *A61F 2/30*     (2006.01)
    *A61F 2/42*     (2006.01)

(52) U.S. Cl.
    CPC ............... *A61F 2002/3082* (2013.01); *A61F 2002/3085* (2013.01); *A61F 2002/30156* (2013.01); *A61F 2002/30179* (2013.01); *A61F 2002/30235* (2013.01); *A61F 2002/30405* (2013.01); *A61F 2002/30576* (2013.01); *A61F 2002/30604* (2013.01); *A61F 2002/30622* (2013.01); *A61F 2002/30777* (2013.01); *A61F 2002/30785* (2013.01); *A61F 2002/30787* (2013.01); *A61F 2002/30841* (2013.01); *A61F 2002/4238* (2013.01); *A61F 2002/448* (2013.01); *A61F 2210/0004* (2013.01); *A61F 2220/0025* (2013.01); *A61F 2230/0023* (2013.01); *A61F 2230/0058* (2013.01); *A61F 2230/0069* (2013.01); *A61F 2310/00017* (2013.01); *A61F 2310/00023* (2013.01); *A61F 2310/00029* (2013.01); *A61F 2310/0097* (2013.01); *A61F 2310/00131* (2013.01); *A61F 2310/00179* (2013.01); *A61F 2310/00329* (2013.01); *A61F 2310/00796* (2013.01)

(56) References Cited

U.S. PATENT DOCUMENTS

| | | | | |
|---|---|---|---|---|
| 2,243,717 A | | 5/1941 | Moreira | |
| 2,414,882 A | | 7/1947 | Longfellow | |
| 2,562,419 A | | 7/1951 | Ferris | |
| 2,675,801 A | | 4/1954 | Bambara et al. | |
| 2,697,433 A | | 12/1954 | Zehnder | |
| 3,076,453 A | * | 2/1963 | Tronzo | 606/67 |
| 3,506,982 A | | 4/1970 | Steffee | |
| 3,694,821 A | | 10/1972 | Moritz | |
| 3,709,218 A | | 1/1973 | Halloran | |
| 3,744,488 A | | 7/1973 | Cox | |
| 4,059,115 A | | 11/1977 | Jumashev et al. | |
| 4,156,943 A | | 6/1979 | Collier | |
| 4,292,964 A | | 10/1981 | Ulrich | |
| 4,341,206 A | | 7/1982 | Perrett et al. | |
| 4,344,190 A | | 8/1982 | Lee et al. | |
| 4,399,813 A | | 8/1983 | Barber | |
| 4,423,721 A | | 1/1984 | Otte et al. | |
| 4,475,545 A | | 10/1984 | Ender | |
| 4,501,269 A | | 2/1985 | Bagby | |
| 4,569,338 A | | 2/1986 | Edwards | |
| 4,612,918 A | | 9/1986 | Slocum | |
| 4,622,959 A | | 11/1986 | Marcus | |
| 4,630,601 A | | 12/1986 | Harder et al. | |
| 4,638,799 A | | 1/1987 | Moore | |
| 4,657,550 A | | 4/1987 | Daher | |
| 4,743,256 A | * | 5/1988 | Brantigan | 128/898 |
| 4,773,402 A | | 9/1988 | Asher et al. | |
| 4,787,378 A | * | 11/1988 | Sodhi | 606/67 |
| 4,790,303 A | | 12/1988 | Steffee | |
| 4,834,757 A | | 5/1989 | Brantigan | |
| 4,846,162 A | | 7/1989 | Moehring | |
| 4,877,019 A | | 10/1989 | Vives | |
| 4,878,915 A | | 11/1989 | Brantigan | |
| 4,898,186 A | * | 2/1990 | Ikada et al. | 606/62 |
| 4,904,261 A | | 2/1990 | Dove et al. | |
| 4,950,270 A | | 8/1990 | Bowman et al. | |
| 4,961,740 A | | 10/1990 | Ray et al. | |
| 4,981,481 A | * | 1/1991 | Kranz et al. | 606/62 |
| 5,034,011 A | | 7/1991 | Howland | |
| 5,034,013 A | | 7/1991 | Kyle et al. | |
| 5,035,697 A | | 7/1991 | Frigg | |
| 5,041,118 A | | 8/1991 | Wasilewski | |
| 5,053,035 A | | 10/1991 | McClaren | |
| 5,066,296 A | | 11/1991 | Chapman et al. | |
| 5,102,414 A | | 4/1992 | Kirsch | |
| 5,108,397 A | | 4/1992 | White | |
| 5,122,141 A | | 6/1992 | Simpson et al. | |
| 5,139,498 A | | 8/1992 | Astudillo Ley | |
| 5,139,500 A | | 8/1992 | Schwartz | |
| 5,147,367 A | | 9/1992 | Ellis | |
| 5,147,402 A | * | 9/1992 | Bohler et al. | 623/16.11 |
| 5,190,551 A | | 3/1993 | Chin et al. | |
| 5,197,961 A | | 3/1993 | Castle | |
| 5,242,444 A | | 9/1993 | MacMillan | |
| 5,298,254 A | | 3/1994 | Prewett et al. | |
| 5,334,205 A | | 8/1994 | Cain | |
| 5,380,325 A | | 1/1995 | Lahille et al. | |
| 5,433,718 A | | 7/1995 | Brinker | |
| 5,443,466 A | | 8/1995 | Shah | |
| 5,458,638 A | | 10/1995 | Kuslich et al. | |
| 5,470,334 A | | 11/1995 | Ross et al. | |
| 5,480,402 A | | 1/1996 | Kim | |
| 5,569,249 A | | 10/1996 | James et al. | |
| 5,591,235 A | | 1/1997 | Kuslich | |
| 5,593,409 A | | 1/1997 | Michelson | |
| 5,609,636 A | | 3/1997 | Kohrs et al. | |
| 5,626,616 A | | 5/1997 | Speece | |
| 5,643,264 A | | 7/1997 | Sherman et al. | |
| 5,645,599 A | | 7/1997 | Samani | |
| 5,658,337 A | * | 8/1997 | Kohrs et al. | 623/17.11 |
| 5,667,510 A | | 9/1997 | Combs | |
| 5,669,909 A | | 9/1997 | Zdeblick et al. | |
| 5,672,178 A | | 9/1997 | Petersen | |
| 5,683,391 A | | 11/1997 | Boyd | |
| 5,709,683 A | | 1/1998 | Bagby | |
| 5,713,904 A | | 2/1998 | Errico et al. | |
| 5,716,358 A | | 2/1998 | Ochoa et al. | |
| 5,725,581 A | | 3/1998 | Brånemark | |
| 5,743,912 A | | 4/1998 | LaHille et al. | |
| 5,759,035 A | | 6/1998 | Ricci | |
| 5,766,174 A | * | 6/1998 | Perry | 606/62 |
| 5,766,261 A | | 6/1998 | Neal et al. | |
| 5,788,699 A | | 8/1998 | Bobst et al. | |
| 5,800,440 A | | 9/1998 | Stead | |
| 5,868,749 A | | 2/1999 | Reed | |
| 5,897,556 A | | 4/1999 | Drewry et al. | |
| 5,928,239 A | | 7/1999 | Mirza | |
| 5,941,885 A | | 8/1999 | Jackson | |
| 5,961,522 A | | 10/1999 | Mehdizadeh | |
| 5,961,554 A | * | 10/1999 | Janson et al. | 623/17.16 |
| 5,968,047 A | | 10/1999 | Reed | |
| 6,010,507 A | | 1/2000 | Rudloff | |
| 6,015,409 A | | 1/2000 | Jackson | |
| 6,053,916 A | | 4/2000 | Moore | |
| 6,056,749 A | | 5/2000 | Kuslich | |
| 6,086,589 A | | 7/2000 | Kuslich et al. | |
| 6,096,080 A | | 8/2000 | Nicholson et al. | |
| 6,120,504 A | | 9/2000 | Brumback et al. | |
| 6,143,031 A | | 11/2000 | Knothe et al. | |
| 6,197,062 B1 | | 3/2001 | Fenlin | |
| 6,210,442 B1 | | 4/2001 | Wing et al. | |
| 6,214,049 B1 | | 4/2001 | Gayer et al. | |
| 6,221,074 B1 | | 4/2001 | Cole et al. | |
| 6,224,607 B1 | | 5/2001 | Michelson | |
| 6,241,732 B1 | | 6/2001 | Overaker et al. | |
| 6,264,657 B1 | | 7/2001 | Urbahns et al. | |
| 6,270,528 B1 | | 8/2001 | McKay | |

(56) References Cited

U.S. PATENT DOCUMENTS

| | | |
|---|---|---|
| 6,287,343 B1 | 9/2001 | Kuslich et al. |
| 6,302,885 B1 | 10/2001 | Essiger |
| 6,302,914 B1* | 10/2001 | Michelson ............... 623/17.16 |
| 6,306,140 B1 | 10/2001 | Siddiqui |
| 6,319,253 B1 | 11/2001 | Ackeret et al. |
| 6,409,768 B1 | 6/2002 | Tepic et al. |
| 6,451,020 B1 | 9/2002 | Zucherman et al. |
| 6,471,707 B1 | 10/2002 | Miller et al. |
| 6,485,518 B1 | 11/2002 | Cornwall et al. |
| 6,497,707 B1 | 12/2002 | Bowman et al. |
| 6,517,541 B1 | 2/2003 | Sesic |
| 6,520,969 B2 | 2/2003 | Lambrecht et al. |
| 6,524,314 B1 | 2/2003 | Dean et al. |
| 6,527,775 B1* | 3/2003 | Warburton ............... 606/62 |
| 6,558,386 B1 | 5/2003 | Cragg |
| 6,565,566 B1 | 5/2003 | Wagner et al. |
| 6,575,899 B1* | 6/2003 | Foley et al. ............... 600/114 |
| 6,575,991 B1 | 6/2003 | Chesbrough et al. |
| 6,579,293 B1* | 6/2003 | Chandran ............... 606/64 |
| 6,582,431 B1 | 6/2003 | Ray |
| 6,595,998 B2 | 7/2003 | Johnson et al. |
| 6,602,293 B1 | 8/2003 | Biermann et al. |
| 6,605,090 B1 | 8/2003 | Trieu et al. |
| 6,607,530 B1 | 8/2003 | Carl et al. |
| 6,620,163 B1 | 9/2003 | Michelson |
| 6,635,059 B2 | 10/2003 | Randall et al. |
| 6,666,868 B2 | 12/2003 | Fallin |
| 6,669,529 B1* | 12/2003 | Scaries ............... 446/397 |
| 6,673,075 B2* | 1/2004 | Santilli ............... 623/17.16 |
| 6,692,501 B2 | 2/2004 | Michelson |
| 6,723,099 B1 | 4/2004 | Goshert |
| 6,740,118 B2 | 5/2004 | Eisermann et al. |
| 6,743,257 B2 | 6/2004 | Castro |
| D493,533 S | 7/2004 | Blain |
| 6,793,656 B1 | 9/2004 | Mathews |
| 6,827,740 B1 | 12/2004 | Michelson |
| 6,984,235 B2 | 1/2006 | Huebner |
| 7,118,579 B2 | 10/2006 | Michelson |
| 7,175,663 B1 | 2/2007 | Stone |
| 7,211,085 B2 | 5/2007 | Michelson |
| 7,223,269 B2 | 5/2007 | Chappuis |
| 7,314,488 B2 | 1/2008 | Reiley |
| 7,335,205 B2 | 2/2008 | Aeschlimann et al. |
| 7,338,500 B2 | 3/2008 | Chappuis |
| 7,452,359 B1 | 11/2008 | Michelson |
| 7,452,369 B2 | 11/2008 | Barry |
| 7,481,831 B2 | 1/2009 | Bonutti |
| 7,527,649 B1 | 5/2009 | Blain |
| 7,534,254 B1 | 5/2009 | Michelson |
| 7,537,616 B1 | 5/2009 | Branch et al. |
| 7,569,054 B2 | 8/2009 | Michelson |
| 7,569,059 B2 | 8/2009 | Cerundolo |
| 7,601,155 B2 | 10/2009 | Petersen |
| 7,648,509 B2 | 1/2010 | Stark |
| 7,686,805 B2 | 3/2010 | Michelson |
| 7,699,852 B2 | 4/2010 | Frankel et al. |
| 7,708,761 B2 | 5/2010 | Petersen |
| 7,727,235 B2 | 6/2010 | Contiliano et al. |
| 7,758,646 B2 | 7/2010 | Khandkar et al. |
| 7,780,704 B2 | 8/2010 | Markworth et al. |
| 7,850,732 B2 | 12/2010 | Heinz |
| 7,857,832 B2 | 12/2010 | Culbert et al. |
| 7,887,565 B2 | 2/2011 | Michelson |
| 7,909,832 B2 | 3/2011 | Michelson |
| 7,922,765 B2 | 4/2011 | Reiley |
| 7,942,879 B2 | 5/2011 | Christie et al. |
| 8,052,728 B2 | 11/2011 | Hestad |
| 8,062,365 B2 | 11/2011 | Schwab |
| 8,066,705 B2 | 11/2011 | Michelson |
| 8,066,709 B2 | 11/2011 | Michelson |
| 8,142,481 B2 | 3/2012 | Warnick |
| 8,317,862 B2 | 11/2012 | Troger et al. |
| 8,398,635 B2 | 3/2013 | Vaidya |
| 8,641,737 B2 | 2/2014 | Matthis et al. |
| 8,672,986 B2 | 3/2014 | Klaue et al. |
| 8,945,190 B2 | 2/2015 | Culbert et al. |
| 8,951,254 B2 | 2/2015 | Mayer et al. |
| 8,951,293 B2 | 2/2015 | Glazer et al. |
| 8,951,295 B2 | 2/2015 | Matityahu et al. |
| 2001/0012942 A1 | 8/2001 | Estes et al. |
| 2001/0046518 A1 | 11/2001 | Sawhney |
| 2001/0047207 A1 | 11/2001 | Michelson |
| 2001/0049529 A1 | 12/2001 | Cachia et al. |
| 2002/0038123 A1* | 3/2002 | Visotsky et al. ............... 606/73 |
| 2002/0049497 A1 | 4/2002 | Mason |
| 2002/0077641 A1 | 6/2002 | Michelson |
| 2002/0082598 A1 | 6/2002 | Teitelbaum |
| 2002/0120275 A1 | 8/2002 | Schmieding et al. |
| 2002/0128652 A1 | 9/2002 | Ferree |
| 2002/0143334 A1* | 10/2002 | Hoffmann et al. ............... 606/67 |
| 2002/0143335 A1 | 10/2002 | von Hoffmann et al. |
| 2002/0151903 A1 | 10/2002 | Takei et al. |
| 2002/0183858 A1 | 12/2002 | Contiliano et al. |
| 2002/0198527 A1 | 12/2002 | Muckter |
| 2003/0018336 A1 | 1/2003 | Vandewalle |
| 2003/0032961 A1* | 2/2003 | Pelo et al. ............... 606/72 |
| 2003/0050642 A1 | 3/2003 | Schmieding et al. |
| 2003/0065332 A1 | 4/2003 | TenHuisen et al. |
| 2003/0074000 A1 | 4/2003 | Roth et al. |
| 2003/0078660 A1 | 4/2003 | Clifford et al. |
| 2003/0083668 A1 | 5/2003 | Rogers et al. |
| 2003/0083688 A1 | 5/2003 | Simonson |
| 2003/0097131 A1 | 5/2003 | Schon et al. |
| 2003/0139815 A1 | 7/2003 | Grooms et al. |
| 2003/0181982 A1 | 9/2003 | Kuslich |
| 2003/0199983 A1 | 10/2003 | Michelson |
| 2003/0229358 A1 | 12/2003 | Errico et al. |
| 2003/0233146 A1 | 12/2003 | Grinberg et al. |
| 2003/0233147 A1 | 12/2003 | Nicholson et al. |
| 2004/0010315 A1 | 1/2004 | Song |
| 2004/0024458 A1 | 2/2004 | Senegas et al. |
| 2004/0034422 A1 | 2/2004 | Errico et al. |
| 2004/0073216 A1 | 4/2004 | Lieberman |
| 2004/0073314 A1 | 4/2004 | White et al. |
| 2004/0082955 A1 | 4/2004 | Zirkle |
| 2004/0087948 A1 | 5/2004 | Suddaby |
| 2004/0106925 A1 | 6/2004 | Culbert |
| 2004/0117022 A1 | 6/2004 | Marnay et al. |
| 2004/0127990 A1 | 7/2004 | Bartish, Jr. et al. |
| 2004/0138750 A1 | 7/2004 | Mitchell |
| 2004/0138753 A1 | 7/2004 | Ferree |
| 2004/0147929 A1 | 7/2004 | Biedermann et al. |
| 2004/0176287 A1 | 9/2004 | Harrison et al. |
| 2004/0176853 A1 | 9/2004 | Sennett et al. |
| 2004/0181282 A1 | 9/2004 | Zucherman et al. |
| 2004/0210221 A1 | 10/2004 | Kozak et al. |
| 2004/0225360 A1 | 11/2004 | Malone |
| 2004/0230305 A1 | 11/2004 | Gorensek et al. |
| 2004/0260286 A1 | 12/2004 | Ferree |
| 2004/0267369 A1 | 12/2004 | Lyons et al. |
| 2005/0015059 A1 | 1/2005 | Sweeney |
| 2005/0015146 A1 | 1/2005 | Louis et al. |
| 2005/0033435 A1 | 2/2005 | Belliard et al. |
| 2005/0049590 A1 | 3/2005 | Alleyne et al. |
| 2005/0055023 A1 | 3/2005 | Sohngen et al. |
| 2005/0075641 A1 | 4/2005 | Singhatat et al. |
| 2005/0080415 A1 | 4/2005 | Keyer et al. |
| 2005/0107878 A1 | 5/2005 | Conchy |
| 2005/0124993 A1 | 6/2005 | Chappuis |
| 2005/0131409 A1 | 6/2005 | Chervitz et al. |
| 2005/0137605 A1 | 6/2005 | Assell et al. |
| 2005/0149192 A1 | 7/2005 | Zucherman et al. |
| 2005/0159749 A1 | 7/2005 | Levy et al. |
| 2005/0165398 A1 | 7/2005 | Reiley |
| 2005/0192572 A1 | 9/2005 | Abdelgany et al. |
| 2005/0228384 A1 | 10/2005 | Zucherman et al. |
| 2005/0246021 A1 | 11/2005 | Ringeisen et al. |
| 2005/0251146 A1 | 11/2005 | Martz et al. |
| 2005/0277940 A1 | 12/2005 | Neff |
| 2006/0036247 A1 | 2/2006 | Michelson |
| 2006/0036251 A1 | 2/2006 | Reiley |
| 2006/0054171 A1 | 3/2006 | Dall |
| 2006/0058793 A1 | 3/2006 | Michelson |
| 2006/0058800 A1 | 3/2006 | Ainsworth et al. |

(56) References Cited

U.S. PATENT DOCUMENTS

| | | |
|---|---|---|
| 2006/0062825 A1 | 3/2006 | Maccecchini |
| 2006/0084986 A1 | 4/2006 | Grinberg et al. |
| 2006/0089656 A1 | 4/2006 | Allard et al. |
| 2006/0111779 A1 | 5/2006 | Petersen |
| 2006/0129247 A1 | 6/2006 | Brown et al. |
| 2006/0142772 A1* | 6/2006 | Ralph et al. ............. 606/76 |
| 2006/0161163 A1 | 7/2006 | Shino |
| 2006/0178673 A1 | 8/2006 | Curran |
| 2006/0217717 A1 | 9/2006 | Whipple |
| 2006/0241776 A1 | 10/2006 | Brown et al. |
| 2006/0271054 A1 | 11/2006 | Sucec et al. |
| 2006/0293662 A1 | 12/2006 | Boyer, II et al. |
| 2007/0027544 A1 | 2/2007 | McCord et al. |
| 2007/0049933 A1 | 3/2007 | Ahn et al. |
| 2007/0066977 A1 | 3/2007 | Assell et al. |
| 2007/0083265 A1 | 4/2007 | Malone |
| 2007/0088362 A1 | 4/2007 | Bonutti et al. |
| 2007/0093841 A1 | 4/2007 | Hoogland |
| 2007/0106383 A1 | 5/2007 | Abdou |
| 2007/0149976 A1 | 6/2007 | Hale et al. |
| 2007/0156144 A1 | 7/2007 | Ulrich et al. |
| 2007/0156241 A1 | 7/2007 | Reiley et al. |
| 2007/0156246 A1 | 7/2007 | Meswania et al. |
| 2007/0161989 A1 | 7/2007 | Heinz et al. |
| 2007/0219634 A1 | 9/2007 | Greenhalgh et al. |
| 2007/0233146 A1 | 10/2007 | Henniges et al. |
| 2007/0250166 A1 | 10/2007 | McKay |
| 2007/0270879 A1 | 11/2007 | Isaza et al. |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0021461 A1 | 1/2008 | Barker et al. |
| 2008/0021480 A1 | 1/2008 | Chin et al. |
| 2008/0065093 A1 | 3/2008 | Assell et al. |
| 2008/0065215 A1 | 3/2008 | Reiley |
| 2008/0109083 A1 | 5/2008 | Van Hoeck et al. |
| 2008/0140082 A1 | 6/2008 | Erdem et al. |
| 2008/0147079 A1 | 6/2008 | Chin et al. |
| 2008/0154316 A1 | 6/2008 | Reiley |
| 2008/0154374 A1 | 6/2008 | Labrom |
| 2008/0161810 A1 | 7/2008 | Melkent |
| 2008/0183204 A1 | 7/2008 | Greenhalgh et al. |
| 2008/0234758 A1 | 9/2008 | Fisher et al. |
| 2008/0255562 A1 | 10/2008 | Gil et al. |
| 2008/0255618 A1 | 10/2008 | Fisher et al. |
| 2008/0255622 A1 | 10/2008 | Mickiewicz et al. |
| 2008/0255664 A1 | 10/2008 | Hogendijk et al. |
| 2008/0255666 A1 | 10/2008 | Fisher et al. |
| 2008/0255667 A1 | 10/2008 | Horton |
| 2008/0275454 A1 | 11/2008 | Geibel |
| 2008/0306554 A1 | 12/2008 | McKinley |
| 2009/0012529 A1 | 1/2009 | Blain et al. |
| 2009/0018660 A1 | 1/2009 | Roush |
| 2009/0024174 A1 | 1/2009 | Stark |
| 2009/0036927 A1 | 2/2009 | Vestgaarden |
| 2009/0043393 A1 | 2/2009 | Duggal et al. |
| 2009/0082869 A1 | 3/2009 | Slemker et al. |
| 2009/0099602 A1 | 4/2009 | Aflatoon |
| 2009/0099610 A1 | 4/2009 | Johnson et al. |
| 2009/0105770 A1 | 4/2009 | Berrevoets et al. |
| 2009/0131986 A1 | 5/2009 | Lee et al. |
| 2009/0138053 A1 | 5/2009 | Assell et al. |
| 2009/0157119 A1 | 6/2009 | Hale |
| 2009/0163920 A1 | 6/2009 | Hochschuler et al. |
| 2009/0187247 A1 | 7/2009 | Metcalf, Jr. et al. |
| 2009/0216238 A1 | 8/2009 | Stark |
| 2009/0270929 A1 | 10/2009 | Suddaby |
| 2009/0287254 A1 | 11/2009 | Nayet et al. |
| 2009/0312798 A1 | 12/2009 | Varela |
| 2009/0324678 A1 | 12/2009 | Thorne et al. |
| 2010/0076502 A1 | 3/2010 | Guyer et al. |
| 2010/0081107 A1 | 4/2010 | Bagambisa et al. |
| 2010/0094290 A1 | 4/2010 | Vaidya |
| 2010/0094295 A1 | 4/2010 | Schnieders et al. |
| 2010/0106194 A1 | 4/2010 | Bonutti et al. |
| 2010/0106195 A1 | 4/2010 | Serhan et al. |
| 2010/0114174 A1 | 5/2010 | Jones et al. |
| 2010/0114317 A1 | 5/2010 | Lambrecht et al. |
| 2010/0145461 A1 | 6/2010 | Landry et al. |
| 2010/0160977 A1 | 6/2010 | Gephart et al. |
| 2010/0191292 A1 | 7/2010 | DeMeo et al. |
| 2010/0280619 A1 | 11/2010 | Yuan et al. |
| 2010/0280622 A1 | 11/2010 | McKinley |
| 2010/0286778 A1 | 11/2010 | Eisermann et al. |
| 2010/0292738 A1 | 11/2010 | Reiley |
| 2011/0029019 A1 | 2/2011 | Ainsworth et al. |
| 2011/0040362 A1 | 2/2011 | Godara et al. |
| 2011/0046737 A1 | 2/2011 | Teisen |
| 2011/0060375 A1 | 3/2011 | Bonutti |
| 2011/0087294 A1 | 4/2011 | Reiley |
| 2011/0087296 A1 | 4/2011 | Reiley et al. |
| 2011/0118785 A1 | 5/2011 | Reiley |
| 2011/0118790 A1 | 5/2011 | Reiley |
| 2011/0118796 A1 | 5/2011 | Reiley et al. |
| 2011/0118841 A1 | 5/2011 | Reiley |
| 2011/0153018 A1 | 6/2011 | Walters et al. |
| 2011/0160866 A1 | 6/2011 | Laurence et al. |
| 2011/0184478 A1 | 7/2011 | Reiley |
| 2011/0196372 A1 | 8/2011 | Murase |
| 2012/0179256 A1 | 7/2012 | Reiley |
| 2013/0131739 A1 | 5/2013 | Reiley |
| 2013/0184769 A1 | 7/2013 | Reiley et al. |
| 2013/0226301 A1 | 8/2013 | Reiley |
| 2013/0237988 A1 | 9/2013 | Mauldin |
| 2013/0238031 A1 | 9/2013 | Reiley |
| 2013/0238093 A1 | 9/2013 | Mauldin et al. |
| 2013/0245763 A1 | 9/2013 | Mauldin |
| 2013/0245764 A1 | 9/2013 | Mauldin |
| 2013/0253654 A1 | 9/2013 | Reiley |
| 2013/0267836 A1 | 10/2013 | Mauldin et al. |
| 2013/0267961 A1 | 10/2013 | Mauldin et al. |
| 2013/0267989 A1 | 10/2013 | Mauldin et al. |
| 2013/0289625 A1 | 10/2013 | Reiley |
| 2013/0296953 A1 | 11/2013 | Mauldin et al. |
| 2014/0222150 A1 | 8/2014 | Reiley |
| 2014/0249589 A1 | 9/2014 | Reiley et al. |
| 2014/0257298 A1 | 9/2014 | Reiley |
| 2014/0257415 A1 | 9/2014 | Reiley |
| 2015/0105828 A1 | 4/2015 | Reckling et al. |

FOREIGN PATENT DOCUMENTS

| | | |
|---|---|---|
| CN | 1909848 A | 2/2007 |
| CN | 101795632 A | 8/2010 |
| EP | 1287796 A1 | 3/2003 |
| JP | 05-176942 A | 7/1993 |
| JP | 2004121841 | 4/2004 |
| JP | 2004512895 | 4/2004 |
| JP | 2004516866 | 6/2004 |
| JP | 2006506181 | 2/2006 |
| WO | WO97/31517 A2 | 8/1997 |
| WO | WO02/38054 | 5/2002 |
| WO | WO03/007839 A2 | 1/2003 |
| WO | WO2004/002344 | 1/2004 |
| WO | WO2005/009729 A2 | 2/2005 |
| WO | WO2006003316 | 1/2006 |
| WO | WO2009/029074 A1 | 3/2009 |

OTHER PUBLICATIONS

Reiley, Mark A.; U.S. Appl. No. 12/357,483 entitled "Systems and methods for the fixation or fusion of bone in the hand and wrist," filed Jan. 22, 2009 (abandoned).

Al-Khayer et al.; Percutaneous sacroiliac joint arthrodesis, a novel technique; J Spinal Disord Tech; vol. 21; No. 5; pp. 359-363; Jul. 2008.

Wise et al.; Minimally invasive sacroiliac arthrodesis, outcomes of a new technique; J Spinal Disord Tech; vol. 21; No. 8; pp. 579-584; Dec. 2008.

Reiley, Mark A.; U.S. Appl. No. 14/162,689 entitled "Systems and methods for the fixation or fusion of bone," filed Jan. 23, 2014.

Mauldin et al.; U.S. Appl. No. 14/216,790 entitled "Systems and (56) References Cited

OTHER PUBLICATIONS methods for implanting bone graft and implant," filed Mar. 17, 2014.
Mesiwala et al.; U.S. Appl. No. 14/216,863 entitled "Implants for spinal fixation or fusion," filed Mar. 17, 2014.
Yerby et al.; U.S. Appl. No. 14/216,938 entitled "Implants for facet fusion," filed Mar. 17, 2014.
Schneider et al.; U.S. Appl. No. 14/217,008 entitled "Systems and methods for removing an implant," filed Mar. 17, 2014.
Yerby et al.; U.S. Appl. No. 14/217,089 entitled "Long implant for sacroiliac joint fusion," filed Mar. 17, 2014.
Mauldin, Richard; U.S. Appl. No. 14/332,294 entitled "Artificial SI Joint," filed Jul. 15, 2014.
Reiley; U.S. Appl. No. 14/488,144 entitled "Systems and methods for the fixation of bone," filed Sep. 16, 2014.
ACUMED; Acutrak Headless Compressioin Screw (product information); 12 pgs; © 2005; retrieved Sep. 25, 2014 from http://www.rcsed.ac.uk/fellows/Ivanrensburg/classification/surgtech/acumed/manuals/acutrak-brochure%200311.pdf.
Peretz et al.; The internal bony architecture of the sacrum; Spine; 23(9); pp. 971-974; May 1, 1998.

\* cited by examiner

SYSTEMS AND METHODS FOR THE FIXATION OR FUSION OF BONE AT OR NEAR A SACROILIAC JOINT

RELATED APPLICATIONS

This application is a continuation-in-part of U.S. patent application Ser. No. 11/653,504, filed Jan. 16, 2007, entitled "Systems and Methods for the Fixation or Fusion of Bone," now U.S. Patent Application Publication No. 2007-0156241-A1 (now abandoned), which is a continuation-in-part of U.S. patent application Ser. No. 11/136,141, filed May 24, 2005, entitled "Systems and Methods for the Fixation or Fusion of Bone," now U.S. Pat. No. 7,922,765, which is a continuation-in-part of U.S. patent application Ser. No. 10/914,629, filed Aug. 9, 2004, entitled "Systems and Methods for the Fixation or Fusion of Bone" (now abandoned). This application is also related to U.S. Provisional Patent Application Ser. No. 61/000,166, filed Oct. 24, 2007 and entitled "Systems and Methods for the Fixation or Fusion of Bone At or Near a Sacroiliac Joint."

FIELD OF THE INVENTION

This application relates generally to the fixation of bone.

BACKGROUND OF THE INVENTION

Many types of hardware are available both for fracture fixation and for the fixation of bones that are to fused (arthrodesed).

Metal and absorbable screws are routinely used to fixate bone fractures and osteotomies. It is important to the successful outcome of the procedure that the screw is able to generate the compressive forces helpful in promoting bone healing.

SUMMARY OF THE INVENTION

The invention provides bone fixation devices and related methods for stabilizing bone segments. The systems and methods include a stem-like structure adapted for passage between adjacent bone segments. At least a portion of the stem-like structure includes a surface that enhances bony in-growth. Boney in-growth into the stem-like structure helps speed up the fusion process or fracture healing time.

According to one aspect of the invention, at least one bone fixation device comprising a stem having a maximum outer diameter is inserted into the sacroiliac joint through a minimally invasive incision path sized approximately at or about the maximum outer diameter of the stem in soft tissue, into the iliac bone, across the sacroiliac joint and into the sacrum. The stem is inserted through the incision path to a position within the sacroiliac joint between the iliac bone and the sacrum, to fuse the sacroiliac joint, without invasive joint preparation, removal of cartilage, or scraping at or near the sacroiliac joint. Desirably, at least a portion of the stem includes a surface permitting bony in-growth.

DESCRIPTION OF THE PREFERRED EMBODIMENT

Although the disclosure hereof is detailed and exact to enable those skilled in the art to practice the invention, the physical embodiments herein disclosed merely exemplify the invention that may be embodied in other specific structure. While the preferred embodiment has been described, the details may be changed without departing from the invention, which is defined by the claims.

Figures 1, 2, 3:
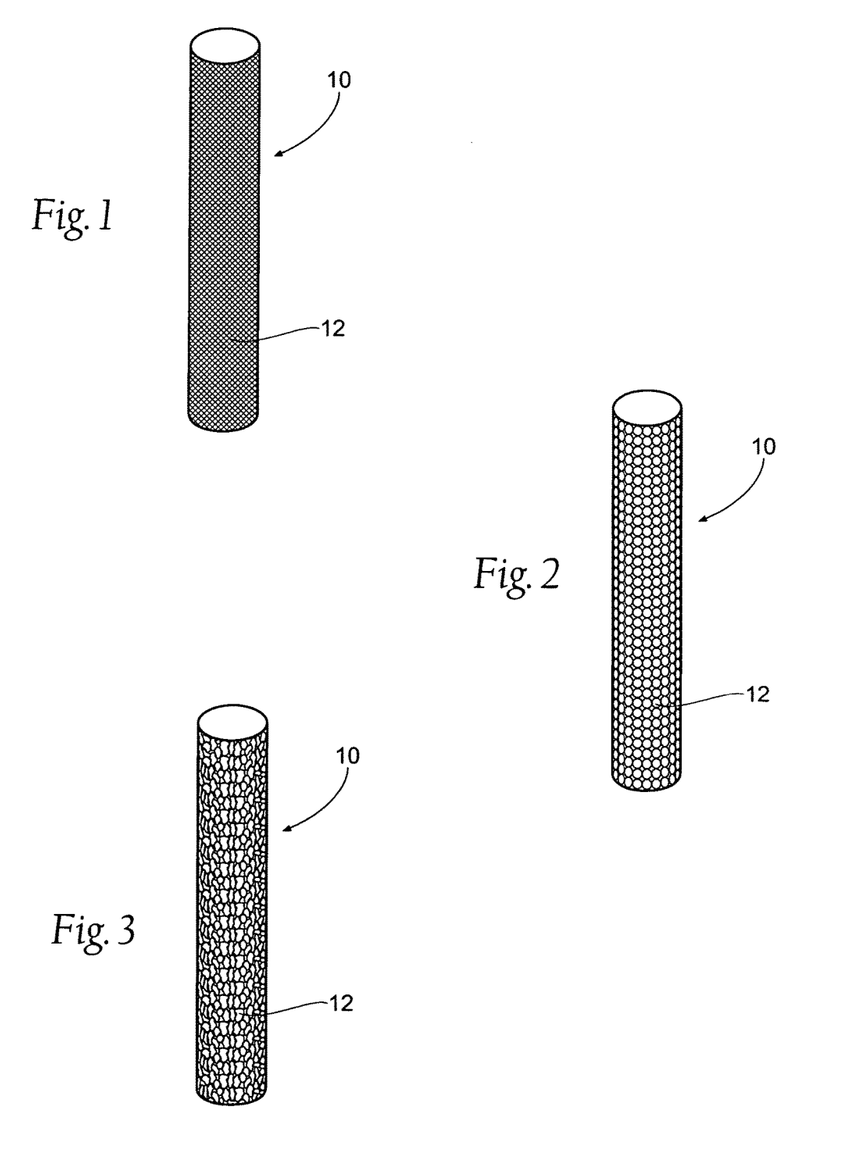
FIG. 1 is a perspective view of a bone fixation stem having a boney in-growth surface of a mesh configuration.
FIG. 2 is a perspective view of an alternative embodiment of a bone fixation stem having a boney in-growth surface of a beaded configuration.
FIG. 3 is a perspective view of an alternative embodiment of a bone fixation stem having a boney in-growth surface of a trabecular configuration.

FIG. 1 shows a device 10 sized and configured for the fixation of bone fractures or for the fixation of bones which are to be fused (arthrodesed). The device 10 comprises an elongated, stem-like structure. The device 10 can be formed—e.g., by machining, molding, or extrusion—from a material usable in the prosthetic arts, including, but not limited to, titanium, titanium alloys, tantalum, chrome cobalt, surgical steel, or any other total joint replacement metal and/or ceramic, sintered glass, artificial bone, any uncemented metal or ceramic surface, or a combination thereof. Alternatively, the device 10 may be formed from a suitable durable biologic material or a combination of metal and biologic material, such as a biocompatible bone-filling material. The device 10 may be molded from a flowable biologic material, e.g., acrylic bone cement, that is cured, e.g., by UV light, to a non-flowable or solid material.

The device 10 can take various shapes and have various cross-sectional geometries. The device 10 can have, e.g., a generally curvilinear (i.e., round or oval) cross-section, or a generally rectilinear cross section (i.e., square or rectangular), or combinations thereof. As will be described in greater detail later, the device 10 can be conical or wedge shaped.

The structure 10 includes surface texturing 12 along at least a portion of its length to promote bony in-growth on its surface. The surface texturing 12 can comprise, e.g., through holes, and/or various surface patterns, and/or various surface textures, and/or pores, or combinations thereof. The device 10 can be coated or wrapped or surfaced treated to provide the surface texturing 12, or it can be formed from a material that itself inherently possesses a surface conducing to bony in-growth, such as a porous mesh, hydroxyapetite, or other porous surface. The device 10 may further be covered with various other coatings such as antimicrobial, antithrombotic, and osteoinductive agents, or a combination thereof. The surface texturing 12 may be impregnated with such agents, if desired.

The configuration of the surface texturing 12 can, of course, vary. By way of examples, FIG. 1 shows the surface 12 as an open mesh configuration; FIG. 2 shows the surface 12 as beaded configuration; and FIG. 3 shows the surface 12 as a trabecular configuration. Any configuration conducive to bony in-growth will suffice.

Figure 4:
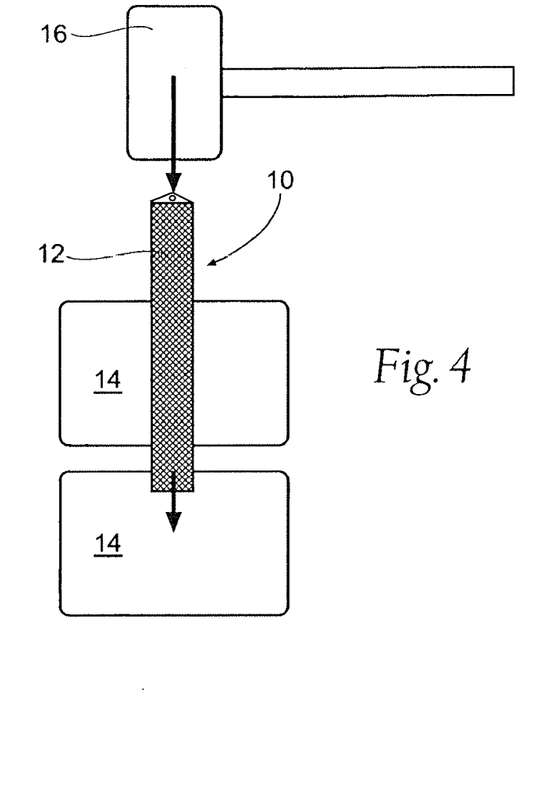
FIG. 4 is a schematic view of a bone fixation stem of the type shown in FIG. 1 being inserted into bone across a fracture line or bone joint.

In use (see FIGS. 4 and 5), the device 10 is inserted into a space between two adjacent bone surfaces, e.g., into a fracture site or between two bones (e.g., adjacent vertebral bodies) which are to be fused together. In FIG. 4, the device 10 is shown being tapped into bone through bone segments 14 (i.e., across a fracture line or between adjacent bones to be fused) with a tap 16. The bone may be drilled first to facilitate insertion of the device 10. The bony in-growth surface 12 along the surface of the device 10 accelerates bony in-growth into the device 10. Boney in-growth into the device 10 helps speed up the fusion process or fracture healing time.

Figure 5:
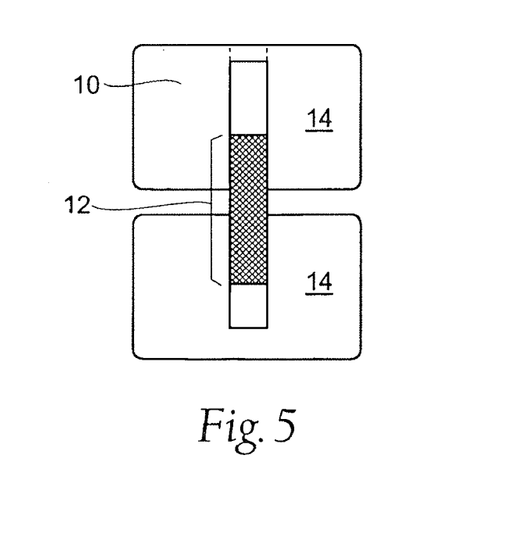
FIG. 5 is a schematic view of a bone fixation stem positioned within bone and illustrating a boney in-growth surface of the stem extending across a fracture line or bone joint.

The bony in-growth surface 12 may cover the entire outer surface of the device 10, as shown in FIG. 4, or the bony in-growth surface 12 may cover just a specified distance on either side of the joint surface or fracture line, as shown in FIG. 5.

The size and configuration of the device 10 can be varied to accommodate the type and location of the bone to be treated as well as individual anatomy.

Figure 6:
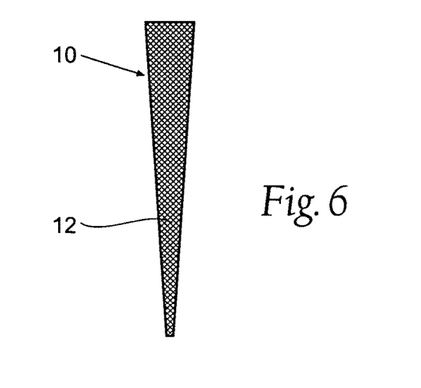
FIG. 6 is a front plan view of an alternative embodiment of a bone fixation stem having a boney in-growth surface in which the stem has a conical configuration.
Figure 7:
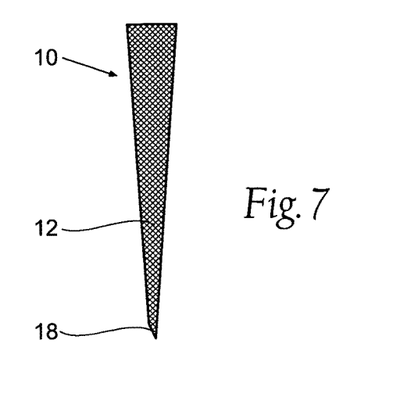
FIG. 7 is front plan view of an alternative embodiment of a bone fixation stem having a boney in-growth surface in which the stem has a beveled distal tip.
Figure 8A:
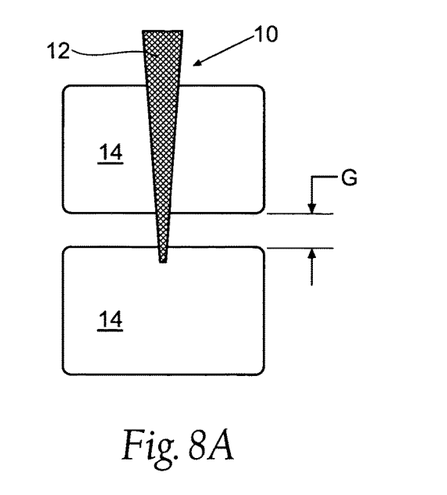
FIGS. 8A and 8B are schematics illustrating the insertion of a conical bone fixation stem of the type shown in FIG. 6 to reduce the gap between bone segments.
Figure 8B:
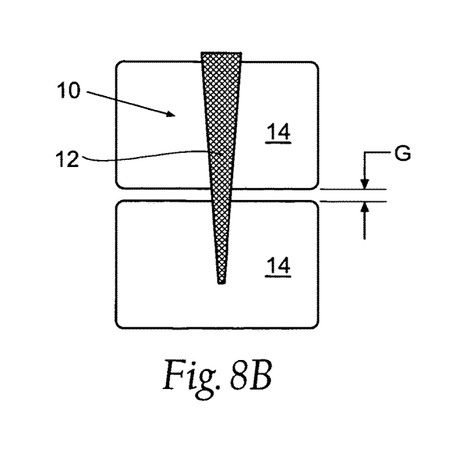

As FIG. 6 shows, the device 10 can be angled or tapered in a conical configuration. The degree of angle can be varied to accommodate specific needs or individual anatomy. A lesser degree of angle (i.e., a more acute angle) decreases the risk of splitting the bone as the device 10 is tapped into the bone or the fracture segments 14. The device 10 may also include a beveled distal tip 18 to further add in insertion of the device 10 into bone, as shown in FIG. 7. As shown in FIGS. 8A and 8B, the conical shape also helps drive the joint surfaces or fracture fragments together, reducing the gap (G) between the bone segments 14.

In FIGS. 9 to 12, the device 10 is cannulated, having a central lumen or throughbore 20 extending through it, to assist in the placement of the device 10 within bone.

Figure 9:
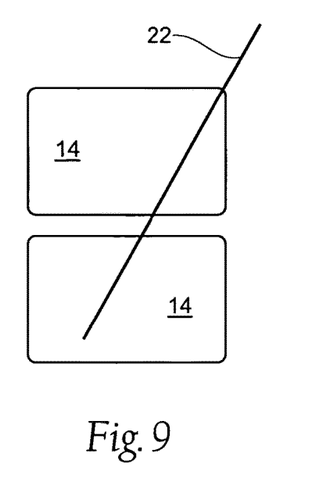
FIG. 9 is a schematic illustrating a guidewire being introduced into bone across bone segments.
Figure 10:
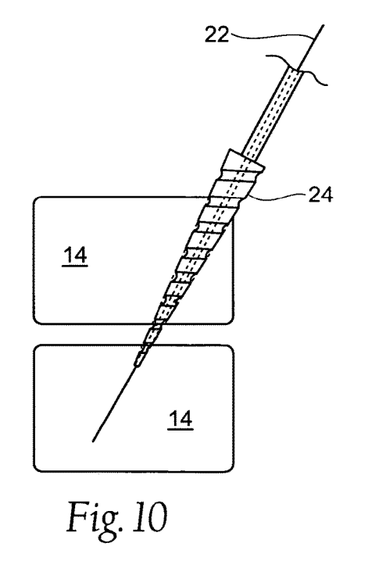
FIG. 10 is a schematic similar to FIG. 9 and illustrating a drill bit being introduced over the guidewire.
Figure 11:
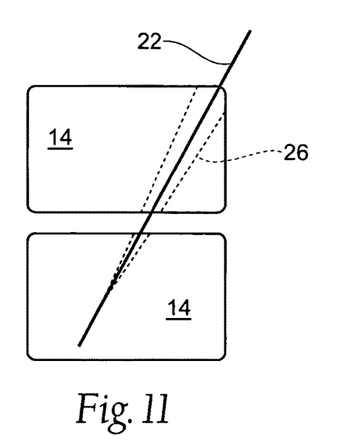
FIG. 11 is a schematic similar to FIG. 10 and illustrating a bore formed in the bone remaining after withdrawal of the drill bit.
Figure 12:
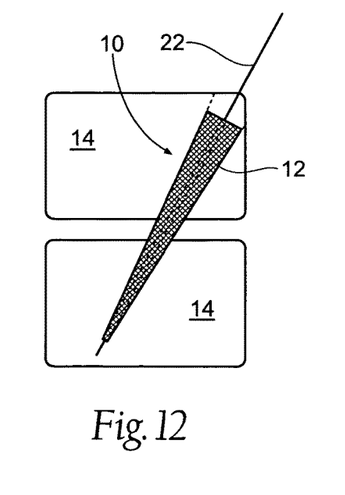
FIG. 12 is a schematic similar to FIG. 11 and illustrating insertion of a bone fixation stem into the pre-formed bore.

In use, the physician can insert a conventional guide pin 22 through the bone segments 14 by conventional methods, as FIG. 9 shows. A cannulated drill bit 24 can then be introduced over the guide pin 22, as seen in FIG. 10. A single or multiple drill bits 24 can be employed to drill through bone fragments or bone surfaces to create a bore 26 of the desired size and configuration. In the illustrated embodiment, the drill bit 24 is sized and configured to create a conical bore 26 similar in size and configuration to the device 10. The bore 26 is desirably sized and configured to permit tight engagement of the device 10 within the bore 26 and thereby restrict movement of the device 10 within the bore 26. The pre-formed bore 26 may be slightly smaller than the device 10, while still allowing the device 10 to be secured into position within the bore 26 by tapping. As seen in FIG. 11, the drill bit 24 is then withdrawn. The device 10 is then inserted into the bore 26 over the guide pin 22, as FIG. 12 shows. The guide pin 22 is then withdrawn.

Alternatively, the device 10 itself can include screw-like threads along the body for screwing the device into place. In the arrangement, the device 10 be self-tapping. Also in this arrangement, the device 10 can be cannulated for use with a guide pin 22, or it need not be cannulated.

Multiple devices 10 may be employed to provide additional stabilization. While the use of multiple devices 10 will now be described illustrating the use of multiple devices 10 of the same size and configuration, it is contemplated that the devices 10 may also be of different size and/or configuration, e.g., one device 10 is of a cylindrical configuration and a second device 10 is of a conical configuration.

Figure 13:
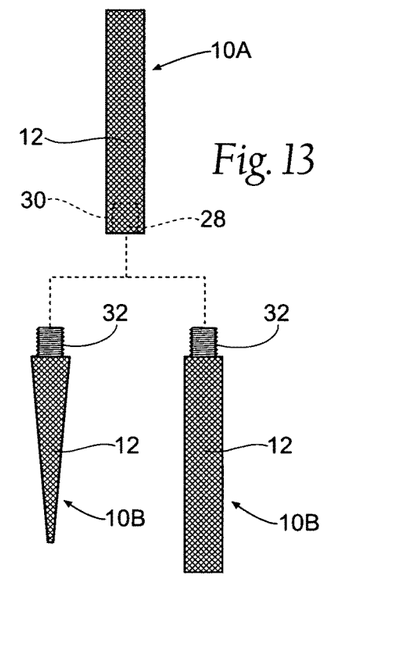
FIG. 13 is an exploded front plan view illustrating the coupling of a pair of bone fixation stems by threaded engagement.

In many cases, it may be desirable to couple a series of devices 10 together, e.g., to provide stabilization over a larger surface area. A series of devices 10 may be coupled together be any suitable means, e.g., by a snap fit engagement or a groove and tab key arrangement. In one embodiment, a series of devices 10 are coupled by threaded engagement. As illustrated in FIG. 13, a first device 10A includes a recess 28 at one end providing a series of internal threads 30. In the illustrated embodiment, the first device 10 is of a cylindrical configuration, but may be of any desired configuration. The internal threads 30 couple with a series of complementary external threads 32 on a second device 10B of a similar or of a different configuration to couple the first and second devices 10A and 10B together.

Figure 14:
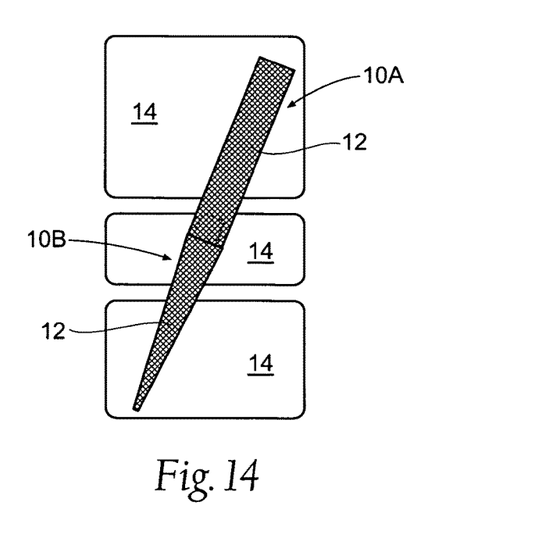
FIG. 14 is a schematic illustrating a pair of bone fixation stems coupled together and inserted into bone across multiple bone segments.

The devices 10A and 10B are desirably coupled together prior to being inserted into the pre-formed bore 26. The series of internal and external threads 30 and 32 provide an interlocking mechanism that permits a series of devices 10 to be stacked and connected to cover a larger area or multiple bone segments 14 (e.g., a bone having multiple fractures) and thereby provides additional stabilization, as seen in FIG. 14.

Figure 15:
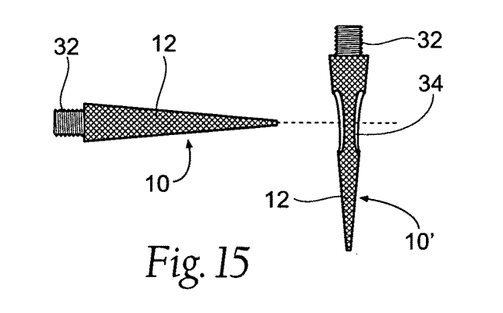
FIG. 15 is a front plan view illustrating passage of a bone fixation stem through a fenestration in another bone fixation stem.

FIG. 15 illustrates another embodiment in which a device 10' includes an opening or fenestration 34 to allow another device 10 to pass through, thereby providing additional stabilization. The fenestration 34 can be sized and configured to permit another device 10 to be passed through the device 10' at virtually any angle. The fenestration 34 can also be sized and configured to limit movement of the second device 10 relative to the second device 10'.

Figure 16:
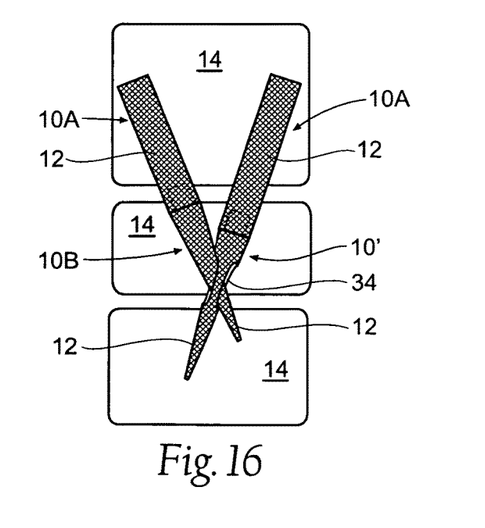
FIG. 16 is a schematic illustrating the placement of a series of bone fixation stems in bone.

In use, and as shown in FIG. 16, the physician taps a first device 10' having a fenestration 34 through the bone segments. A second device 10 is then inserted (e.g., by tapping) through the fenestration 34 of the first device 10' into place.

It is further contemplated that device 10' may also be adapted for coupling with another device 10A (e.g., by a series of external and internal threads), permitting the devices 10' and 10A to be additionally stacked and connected, as also shown in FIG. 16.

Arthrodesis of the Sacroiliac Joint

Figure 17:
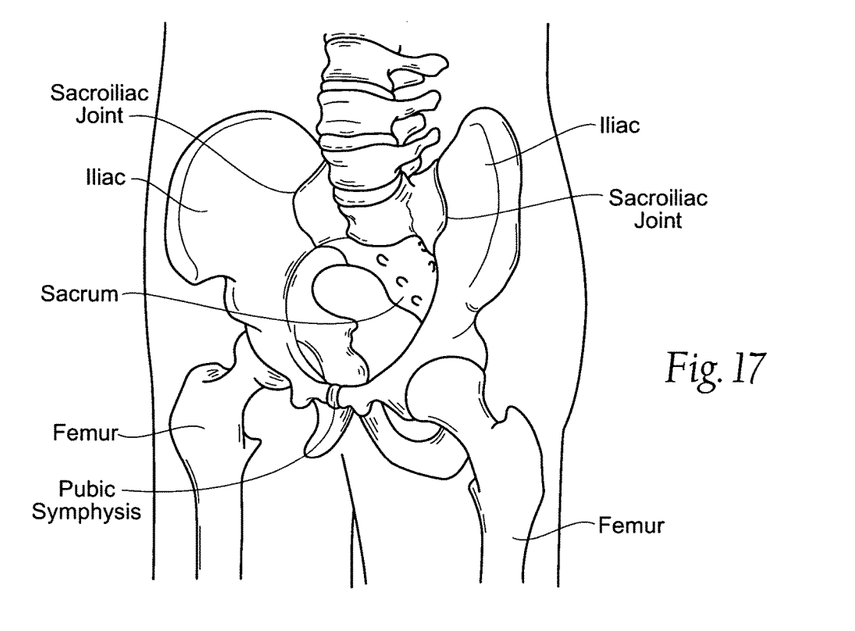
FIG. 17 is a lateral anterior anatomic view of bones in the hip region of the body, showing the iliac bones, the sacrum, and the sacroiliac joint therebetween.

As shown in FIG. 17, the human hip girdle is made up of three large bones joined by three relatively immobile joints. One of the bones is called the sacrum and it lies at the bottom of the lumbar spine, where it connects with the L5 vertebra. The other two bones are commonly called "hip bones" and are technically referred to as the right ilium and the left ilium. The sacrum connects with both hip bones at the sacroiliac (SI) joint.

The sacroiliac joint functions in the transmission of forces from the spine to the lower extremities, and vice-versa. Sacroiliac joint fusion is typically indicated as a surgical treatment for degenerative sacroiliitis, inflammatory sacroiliitis, iatrogenic instability of the sacroiliac joint, osteitis condensans ilii, or traumatic fracture dislocation of the pelvis.

Currently, screw and screw with plates are used for sacro-iliac fusion. At the same time the cartilage has to be removed from the "synovial joint" portion of the SI joint. This requires a large incision to approach the damaged, subluxed, dislocated, fractured, or degenerative joint.

Figure 18:
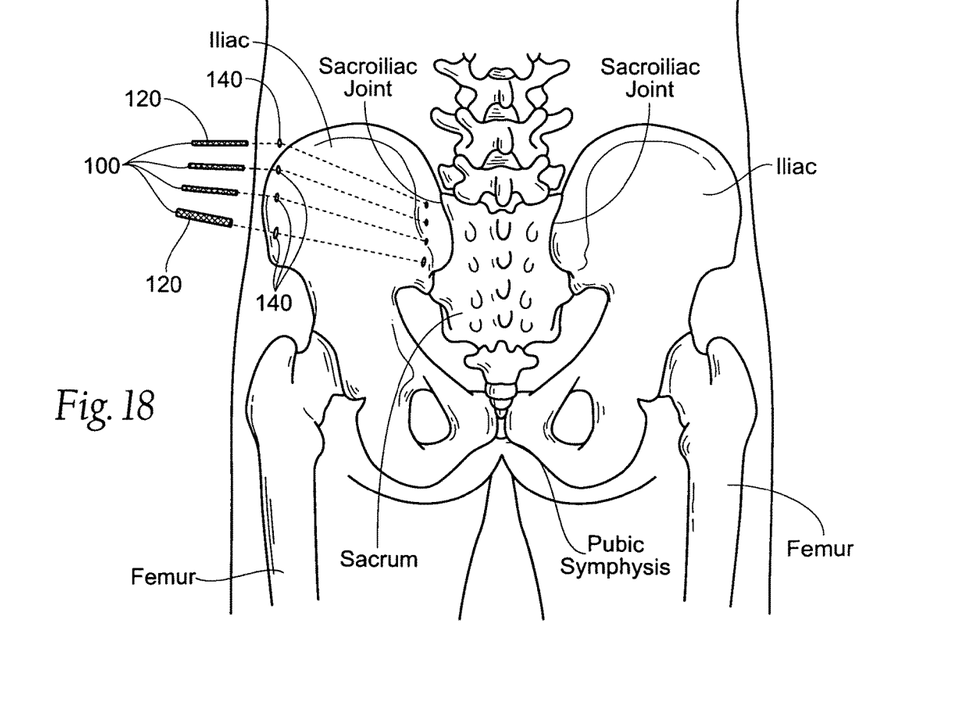
FIG. 18 is a posterior anatomic view of the hip region shown in FIG. 17, showing the incision paths for inserting one or more bone fixation devices into the sacroiliac joint through soft tissue, into the iliac bone, across the sacroiliac joint and into the sacrum.
Figure 19:
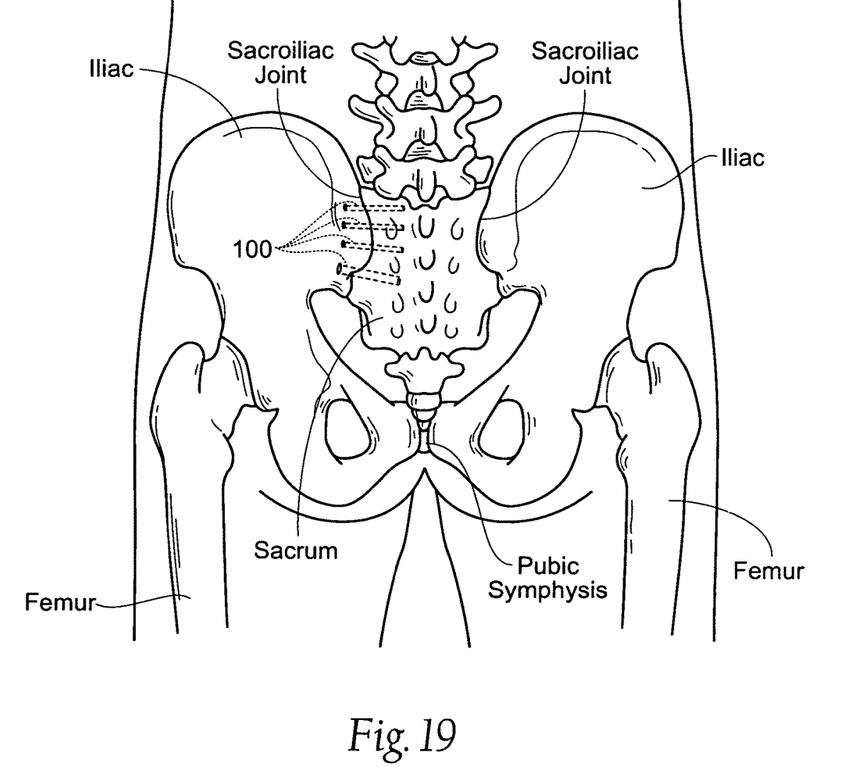
FIG. 19 is a posterior anatomic view as shown in FIG. 18, after insertion of the one or more bone fixation devices into the sacroiliac joint, to fuse the sacroiliac joint.

FIGS. 18 and 19 show one or more devices 100, as previously described and shown, e.g., in FIG. 1, each of which is sized and configured for the fusion (arthrodesis) of the sacro-iliac joint. As previously described, each device 100 comprises an elongated, stem-like structure. Each device 100 can be formed—e.g., by machining, molding, or extrusion—from a material usable in the prosthetic arts, including, but not limited to, titanium, titanium alloys, tantalum, chrome cobalt, surgical steel, or any other total joint replacement metal and/or ceramic, sintered glass, artificial bone, any uncemented metal or ceramic surface, or a combination thereof. Alternatively, each device 100 may be formed from a suitable durable biologic material or a combination of metal and biologic material, such as a biocompatible bone-filling material. The device 100 may be molded from a flowable biologic material, e.g., acrylic bone cement, that is cured, e.g., by UV light, to a non-flowable or solid material.

A given device 100 can take various shapes and have various cross-sectional geometries. A given device 100 can have, e.g., a generally curvilinear (i.e., round or oval) cross-section, or a generally rectilinear cross section (i.e., square or rectangular), or combinations thereof. A given device 100 can be conical or wedge shaped. The devices 100 used for a given arthrodesis can be of different sizes and shapes, depending upon the anatomic conditions encountered.

One or more of the devices 100 (see FIG. 18) desirably includes surface texturing 120 along at least a portion of its length to promote bony in-growth on its surface, as previously described. The surface texturing 120 can comprise, e.g., through holes, and/or various surface patterns, and/or various surface textures, and/or pores, or combinations thereof. The device 100 can be coated or wrapped or surfaced treated to provide the surface texturing 120, or it can be formed from a material that itself inherently possesses a surface conducing to bony in-growth, such as a porous mesh, hydroxyapetite, or other porous surface. The device 100 may further be covered with various other coatings such as antimicrobial, antithrombotic, and osteoinductive agents, or a combination thereof. The surface texturing 120 may be impregnated with such agents, if desired.

One or more of the devices 100 are individually inserted in a minimally invasive fashion through an insertion path 140 in the soft tissue, into the respective iliac bone, across the respective sacroiliac joint and into the sacrum, as FIGS. 18 and 19 show. Conventional tissue access tools, obturators, cannulas, and/or drills can be used for this purpose. No joint preparation, removal of cartilage, or scraping are required before formation of the insertion path or insertion of the device 100, so an minimally invasive insertion path sized approximately at or about the maximum outer diameter of the device 100 need be formed.

In a representative procedure, one to six, or perhaps eight, devices 100 might be needed, depending on the size of the patient and the size of the devices 100.

The described method comprises providing at least one device 100 comprising a stem having a maximum outer diameter. The method creates a minimally invasive incision path sized approximately at or about the maximum outside diameter through soft tissue, into the iliac bone, across the sacroiliac joint and into the sacrum. The method includes, without further joint preparation, removal of cartilage, or scraping at or near the sacroiliac joint, inserting the stem through the incision path to a position within the sacroiliac joint between the iliac bone and the sacrum, to fuse the sacroiliac joint. Preferably, at least a portion of the stem includes a surface permitting bony in-growth.

After installation, the patient would be advised to prevent loading of the sacroiliac joint while fusion occurs. This could be a six to twelve week period or more, depending on the health of the patient and his or her adherence to post-op protocol.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

I claim:

1. A joint fusion device, the joint fusion device comprising:
   an elongated, stem-like device having a triangular cross section free of external screw threads and lateral fenestrations, the device being sized and configured for placement to fuse a sacroiliac joint, which lies between an iliac bone and a sacrum, in response to an axially applied, non-rotational force, the elongated, stem-like device having an exterior surface treated to provide bony in-growth and/or on-growth upon placement, wherein the elongated, stem-like device is formed from one or more materials selected from a group consisting of titanium, titanium alloys, tantalum, chrome cobalt, and surgical steel, wherein the triangular cross section of the elongated, stem-like device is configured to inhibit movement of the sacroiliac joint without the use of an additional component transversely intersecting the device through a lateral fenestration, wherein the elongated, stem-like device has a minimum length greater than a thickness of the iliac bone at the sacroiliac joint.

2. A joint fusion device according to claim 1 further comprising a porous surface conducive to bony in-growth.

3. A joint fusion device according to claim 2 wherein the porous surface is formed by a coating.

4. A joint fusion device according to claim 1 further comprising hydroxyapatite.

5. A joint fusion device according to claim 1, wherein the elongated, stem-like device comprises a lumen to accommodate close fitting passage over a guide pin during placement.

6. A joint fusion device according to claim 1, wherein the elongated, stem-like device has a maximum length less than a distance between a lateral surface of the iliac bone and a midline of sacral vertebral bodies.

7. A joint fusion device, the joint fusion device comprising:
an elongated, stem-like device having a triangular cross section free of external screw threads and lateral fenestrations, the device being sized and configured for placement to fuse a sacroiliac joint, which lies between an iliac bone and a sacrum, in response to an axially applied, non-rotational force, the elongated, stem-like device having an exterior surface treated to provide bony in-growth and/or on-growth upon placement, wherein the elongated, stem-like device is formed from one or more materials selected from a group consisting of titanium, titanium alloys, tantalum, chrome cobalt, and surgical steel, wherein the triangular cross section of the elongated, stem-like device is configured to inhibit movement of the sacroiliac joint without the use of an additional component transversely intersecting the device through a lateral fenestration, wherein the elongated, stem-like device has a maximum length less than a distance between a lateral surface of the iliac bone and a midline of sacral vertebral bodies.

8. A joint fusion device, the joint fusion device comprising:
an elongated, stem-like device having a triangular cross section free of external screw threads and lateral fenestrations, the device being sized and configured for placement to fuse a sacroiliac joint, which lies between an iliac bone and a sacrum, in response to an axially applied, non-rotational force, the elongated, stem-like device having an exterior surface treated to provide bony in-growth upon placement, wherein the elongated, stem-like device is formed from one or more materials selected from a group consisting of titanium, titanium alloys, tantalum, chrome cobalt, and surgical steel, wherein the triangular cross section of the elongated, stem-like device is configured to inhibit movement of the sacroiliac joint without the use of an additional component transversely intersecting the device through a lateral fenestration, wherein the elongated, stem-like device has a length that is approximately equal to a distance between a lateral surface of the iliac bone and a dorsal sacral foramina of the sacrum.

* * * * *